US010557742B2

(12) United States Patent
Saville et al.

(10) Patent No.: US 10,557,742 B2
(45) Date of Patent: Feb. 11, 2020

(54) SYSTEM, DEVICE AND METHOD FOR MONITORING THE LIQUID VOLUME IN A HYDRATION PACK

(71) Applicant: Andrew Saville, Markyate (GB)

(72) Inventors: Andrew Saville, Markyate (GB); Yogesh Dubey, Mysore (IN); M. Gopi Naga Bharath, Mysore (IN); Sujatha Pujar Manjunatha, Mysore (IN)

( * ) Notice: Subject to any disclaimer, the term of this patent is extended or adjusted under 35 U.S.C. 154(b) by 49 days.

(21) Appl. No.: 15/779,248

(22) PCT Filed: Nov. 23, 2016

(86) PCT No.: PCT/GB2016/053674
§ 371 (c)(1),
(2) Date: May 25, 2018

(87) PCT Pub. No.: WO2017/089792
PCT Pub. Date: Jun. 1, 2017

(65) Prior Publication Data
US 2018/0372524 A1    Dec. 27, 2018

(30) Foreign Application Priority Data

Nov. 27, 2015  (GB) .................................. 1520985.1
Aug. 19, 2016  (GB) .................................. 1614225.9

(51) Int. Cl.
*G01F 23/18*     (2006.01)
*A45F 3/20*      (2006.01)
(Continued)

(52) U.S. Cl.
CPC ................ *G01F 23/18* (2013.01); *A45F 3/20* (2013.01); *A61B 5/4875* (2013.01); *G01F 22/00* (2013.01);
(Continued)

(58) Field of Classification Search
CPC ............................................. G01F 23/14–185
See application file for complete search history.

(56) References Cited

U.S. PATENT DOCUMENTS 9,138,091 B2 *  9/2015  Zhao ...................... A47G 23/16
2005/0016267 A1  1/2005  Doorhy et al.
(Continued)

FOREIGN PATENT DOCUMENTS

CN    203851961 U    7/2016
EP    1310778 A1    5/2003
WO    2009/134146 A1    11/2009

OTHER PUBLICATIONS

Search Report for Application GB1520985.1 dated Apr. 29, 2016.
(Continued)

*Primary Examiner* — Nathaniel J Kolb
(74) *Attorney, Agent, or Firm* — Thomas | Horstemeyer, LLP

(57) ABSTRACT

A system for monitoring the volume of fluid in a hydration pack comprises a monitoring unit which is attached to an output of the hydration pack and to a feed tube. The monitoring unit comprises a pressure sensor and a tilt sensor. The pressure sensor obtains a measure of pressure of fluid within the hydration pack that may be used to estimate remaining fluid in the hydration pack. The tilt sensor is able to provide adjustment parameters tor adjusting for changes in pressure due to tilt of the hydration pack. An application on a mobile telephone provides a user with an indication of remaining liquid in the hydration pack. The application provides a visual indication of remaining fluid and may also provide an indication of rate of consumption. The application may also calibrate the system, enabling the system to be fitted to existing hydration pack assemblies.

20 Claims, 15 Drawing Sheets

(51) Int. Cl.
   *A61B 5/00* (2006.01)
   *G01F 25/00* (2006.01)
   *G01F 22/00* (2006.01)
   *G01F 23/00* (2006.01)
   *A45F 3/16* (2006.01)
   *G01P 15/08* (2006.01)

(52) U.S. Cl.
   CPC .... *G01F 25/0084* (2013.01); *A45F 2003/166* (2013.01); *G01F 23/0076* (2013.01); *G01P 15/0802* (2013.01)

(56) References Cited

U.S. PATENT DOCUMENTS

| | | | |
|---|---|---|---|
| 2008/0053255 A1 | 3/2008 | Furey et al. | |
| 2011/0077876 A1* | 3/2011 | Ellingsen | B01L 3/0293 |
| | | | 702/55 |
| 2011/0146425 A1 | 6/2011 | Furey et al. | |
| 2012/0097567 A1* | 4/2012 | Zhao | A47G 23/16 |
| | | | 206/459.1 |
| 2013/0029374 A1 | 1/2013 | Eberheim | |
| 2016/0022209 A1* | 1/2016 | Fraisl | A45F 3/16 |
| | | | 600/590 |
| 2017/0336240 A1* | 11/2017 | Daneyshar | G01F 23/14 |

OTHER PUBLICATIONS

International Search Report and Written Opinion for PCT/GB2016/053674 dated Mar. 17, 2017.
Letter to World Intellectual Property Organization, referencing PCT/GB2016/053674, dated May 21, 2018.

\* cited by examiner

SYSTEM, DEVICE AND METHOD FOR MONITORING THE LIQUID VOLUME IN A HYDRATION PACK

CROSS-REFERENCE TO RELATED APPLICATIONS

The application is the 35 U.S.C. § 371 national stage application of PCT Application No. PCT/GB2016/053674, filed Nov. 23, 2016, entitled "SYSTEM, DEVICE AND METHOD FOR MONITORING THE LIQUID VOLUME IN A HYDRATION PACK", where the PCT claims priority to and the benefit of GB Patent Application No. 1520985.1, filed Nov. 27, 2015, and GB Patent Application No. 1614225.9, filed Aug. 19, 2016, all of which being incorporated by reference in their entireties herein.

FIELD OF THE INVENTION

The present invention relates to a system for and method of monitoring a hydration pack and in particular the volume of liquid in the pack. The invention is particularly useful in assisting athletes and sports people to maintain adequate hydration levels while performing physical activities. It can also prevent hikers, runners, bikers and other sports people from running out of water unknowingly in circumstances where replenishment is unavailable, which can currently be a significant problem and potentially dangerous.

BACKGROUND OF THE INVENTION

U.S. Patent Publication No. 2011/0077876 discloses a tap for mounting on a container containing liquid, such as a wine box, a container containing medicine or a chemical, which tap comprises a sensor arranged on or in the tap for determining the outflow of liquid as a function of dispensing time and outflow characteristics. A display indicates the remaining amount of liquid in the container. The sensor may be a pressure sensor.

U.S. Patent Publication No. 2012/0097567 discloses an apparatus for managing the liquid volume in a container. The apparatus comprises a detector for detecting liquid volume changes in the container during a first preset period, a first determiner for determining whether the changes are lower than the first preset threshold value and a presenter for presenting the first prompt information in the case of the changes being lower than the preset threshold value. The device may include a pressure sensor and a tilt sensor.

It has long been recognized that it is important to maintain adequate levels of hydration particularly when carrying out physical exercise such as sport, hiking and so on. Even low levels of dehydration can have adverse physiological consequences. For instance, a 2% loss in bodyweight can reduce performance by 10-20%. A loss of fluid in excess of 3-5% of body weight reduces aerobic exercise performance noticeably and impairs reaction time, judgement, concentration and decision making. Dehydration can also place a strain on the cardiovascular system and can lead to heat stress and the inability of the body to adjust temperature by the normal sweat mechanisms.

Taking an excessive amount of fluid at any period, whether before the activity, during or after, often fails to ensure adequate hydration as the body is not able to store excess fluid or replenish lost fluid sufficiently quickly. It is best to take small amounts of fluids regularly over the course of the activity. For this purpose, athletes and others will often carry a source of fluid, traditionally in the form of a drinking bottle or cup but more recently by way of a hydration pack which can be kept in a backpack or similar bag. Hydration packs, or bladders as they are sometimes called, have proven very popular as they are comfortable to carry, are conformable in terms of shape, and have a low empty weight. A problem with such hydration packs, and any other liquid container which is flexible or not generally seen when used, is that it is difficult for the user to tell how much fluid they have consumed and how much fluid remains in the container. This results in difficulties in pacing fluid intake and as a result risks inadequate hydration during the period. It is not uncommon for such hydration packs to be used in environments where a ready supply of drinkable water is not available. In such circumstances, should the user run out of water this can cause dehydration and be potentially dangerous.

Flow meters are known for attachment to the outlet tube of a hydration pack but these can only provide a rough indication of fluid consumed, dependent upon the quality of fluid flowing through the outlet tube. A flow meter is not able to measuring remaining fluid in the pack.

A problem with hydration packs is that they are typically very flexible and may be held or carried in a variety of different ways by the user, making it difficult to obtain an accurate measurement of fluid in the pack.

SUMMARY OF THE INVENTION

The present invention seeks to provide a system and method of monitoring a hydration pack and in particular for monitoring the amount of fluid in the pack and for providing an indication of this. The system and method may also provide an indication of fluid consumption.

According to an aspect of the present invention, there is provided a system for monitoring the amount of fluid in a hydration unit having a fluid outlet, the system including:

a monitoring unit including a fluid chamber, an inlet port attachable to a fluid outlet of a hydration unit, an outlet port for attachment to a feed tube, and a pressure sensor mounted to the monitoring unit and in pressure communication with the fluid chamber, a tilt sensor operable to determine angle of tilt of the hydration unit;

a controller in use coupled to the pressure sensor and to the tilt sensor, for obtaining a pressure sensor signal therefrom, the controller being operable to determine from the pressure sensor signal an indication of volume of fluid in the hydration unit, and to calibrate the pressure measurements on the basis of detected tilt angle; and a user interface coupled to the controller and operable to provide an indication of volume of fluid in the hydration unit.

Obtaining a reliable indication of the volume of fluid, typically water or an isotonic liquid, from a hydration unit can often be difficult. The inventors have discovered that a reliable indication can be derived from the pressure of fluid at the outlet of the hydration unit. Typically, the outlet is located at or proximate the base of the chamber of the hydration unit and pressure can therefore provide a useful indication of fluid volume. With an accurate indication of the amount of liquid remaining in the hydration unit the user can pace the intake of liquid, to ensure not only adequate hydration but also to ensure that the user does not run out of liquid during the activity. The latter is particularly beneficial in cases where the activity involves long periods of exercise or other physical exertion and also in circumstances where there is no readily available supply of replenishment liquid (typically water).

With some hydration units and for some uses, the hydration unit may not be held vertical or in a near vertical orientation, with the result that a pressure measurement alone may become inaccurate. By obtaining a measure of tilt of the unit, the effects of tilt can be accounted for, for instance by an appropriate calibration coefficient.

The tilt sensor is advantageously mounted to the monitoring unit. The tilt sensor is preferably an accelerometer.

In some embodiments a valve (preferably electronically controlled) may be provided for closing the outlet port of the monitoring unit so as to isolate the outlet port from any back pressure from the feed tube. This can be advantageous in arrangements where there is no separate drinking valve at the distal end of the feed tube. Where a drinking valve is provided, the latter can prevent any back pressure from the feed tube altering the pressure reading from the pressure sensor.

In a practical embodiment, there is provided a fixation element for fixing the monitoring unit to the hydration unit. The fixation element may be or include an adhesive member. This allows the system to be retrofitted to a hydration unit. Furthermore, it allows for the monitoring unit to be attached securely to the hydration unit, preferably in an optimal orientation. Once fixed, any tilt indication given by the tilt sensor will be consistent with tilting of the hydration unit.

In some embodiments, the controller is mounted to the monitoring unit. In this case, there is preferably provided a communications unit coupled to the controller and operable to send and/or receive data between the controller and the user interface. The communications unit advantageously includes a wireless transponder, although may also be a wire link. In the preferred embodiments, the communications unit includes a Bluetooth, RF or Wi-Fi transponder.

Advantageously, the controller includes a database of calibration values for calibrating the sensed fluid pressure.

In the preferred embodiment, the controller is operable to obtain a sequence of pressure measurements and to determine therefrom fluid consumption.

Preferably, the user interface is an application or a program for a mobile telephone, watch or other smart device.

According to another aspect of the present invention, there is provided a device for monitoring the amount of fluid in a hydration unit, including:

a monitoring unit including a fluid chamber, an inlet port attachable to a fluid outlet of a hydration unit, and an outlet port for attachment to a feed tube;

a pressure sensor mounted to the monitoring unit and in pressure communication with the fluid chamber;

a tilt sensor mounted to the monitoring unit, the tilt sensor being operable to determine angle of tilt of the hydration unit.

The device preferably includes a controller mounted to the monitoring unit and connected to the pressure sensor for obtaining a pressure sensor signal therefrom, the controller being operable to determine from the pressure sensor signal an indication of volume of fluid in the hydration unit and to compensate for deviations in pressure measurements caused by tilt of the hydration unit. The controller may include a database of calibration values for calibrating the indication of volume derived from the sensed pressure. Preferably, the controller is operable to obtain a sequence of pressure measurements and to determine therefrom fluid consumption.

Preferably, the tilt sensor is an accelerometer.

There may be provided a communications unit connected to the controller and operable to send from and/or receive data to the controller. The communications unit preferably includes a wireless transponder, such as a Bluetooth, RF or Wi-Fi transponder.

In some embodiments, the inlet port is in the form of a replaceable adaptor to fit different designs of hydration unit.

In some embodiments, the device includes a connection hose for coupling between the inlet port of the monitoring unit and the outlet port of the hydration unit.

According to another aspect of the present invention, there is provided a hydration unit including a monitoring system or device as taught herein. The unit may be a hydration pack, pouch, or bladder.

In some embodiments, the device may be built-in to a hydration unit.

In some embodiments, the monitoring unit is integral with the hydration unit.

In a preferred embodiment, the inlet port includes a first tubular element including an internal diameter adapted to fit over the outlet port of the hydration unit.

Preferably, the tubular element is made of resilient material, providing a water-tight connection between the outlet port of the hydration unit and the monitoring unit.

In a preferred embodiment, the outlet port includes a second tubular element configured to fit within the feed tube and providing a water-tight connection between the monitoring unit and the feed tube.

Preferably, the second tubular element includes at least one circumferential rib.

There is also described a device for monitoring the amount of fluid in a hydration unit, the hydration unit including a flexible container for holding hydration fluid, the container having an outlet element and a feed tube; the device including a housing within which there is provided a fluid chamber, an inlet port provided with a tubular element for attachment to the outlet of the hydration unit, and an outlet port including an outlet tubular element for attachment to the feed tube, such that the device in use is disposed between the outlet of the hydration pack and inlet of the feed tube; the device including a pressure sensor mounted thereto and in pressure communication with the fluid chamber.

There is also described a system for monitoring the amount of fluid in a hydration unit, the container having a fluid outlet, the system including:

a monitoring unit including a fluid chamber, an inlet port attachable to a fluid outlet of a hydration unit, an outlet port for attachment to a feed tube, and a pressure sensor mounted to the monitoring unit and in pressure communication with the fluid chamber;

a controller in use coupled to the pressure sensor for obtaining a pressure sensor signal therefrom, the controller being operable to determine from the pressure sensor signal an indication of volume of fluid in the hydration unit; and a user interface coupled to the controller and operable to provide an indication of volume of fluid in the hydration unit.

Other features, aspects and advantages of the teachings herein will become apparent in the specific description which follows.

BRIEF DESCRIPTION OF THE DRAWINGS

Embodiments of the present invention are described below, by way of example only, with reference to the accompanying drawings, in which.

DETAILED DESCRIPTION

In summary, the embodiments described herein provide a system and method for monitoring the amount of water or other liquid present in a hydration unit, typically a hydration pack or bladder. The preferred system is designed to measure the pressure and orientation of the hydration unit and upload the readings to a mobile telephone. The monitoring system uses a pressure sensor to detect pressure at the pack's outlet, typically at the base or bottom of the hydration unit, on the basis of which it calculates the volume of liquid in the hydration unit. An accelerometer may be used to compensate for variations in pressure caused by the pack's orientation. There may also be provided in some embodiments a valve (preferably electronically controlled) for closing the outlet of the apparatus, to avoid coupling the feed tube column pressure (which can vary based on feed tube position position). In the preferred embodiment, a mobile application (a program) estimates the volume of water within the pack based on the pressure and accelerometer readings and represent the volume in graphical format. The mobile application may also configure and calibrate the device. In other embodiments, the application may constitute solely the user interface, with the controller being a component of a monitoring unit attached to the hydration pack.

Figure 1:
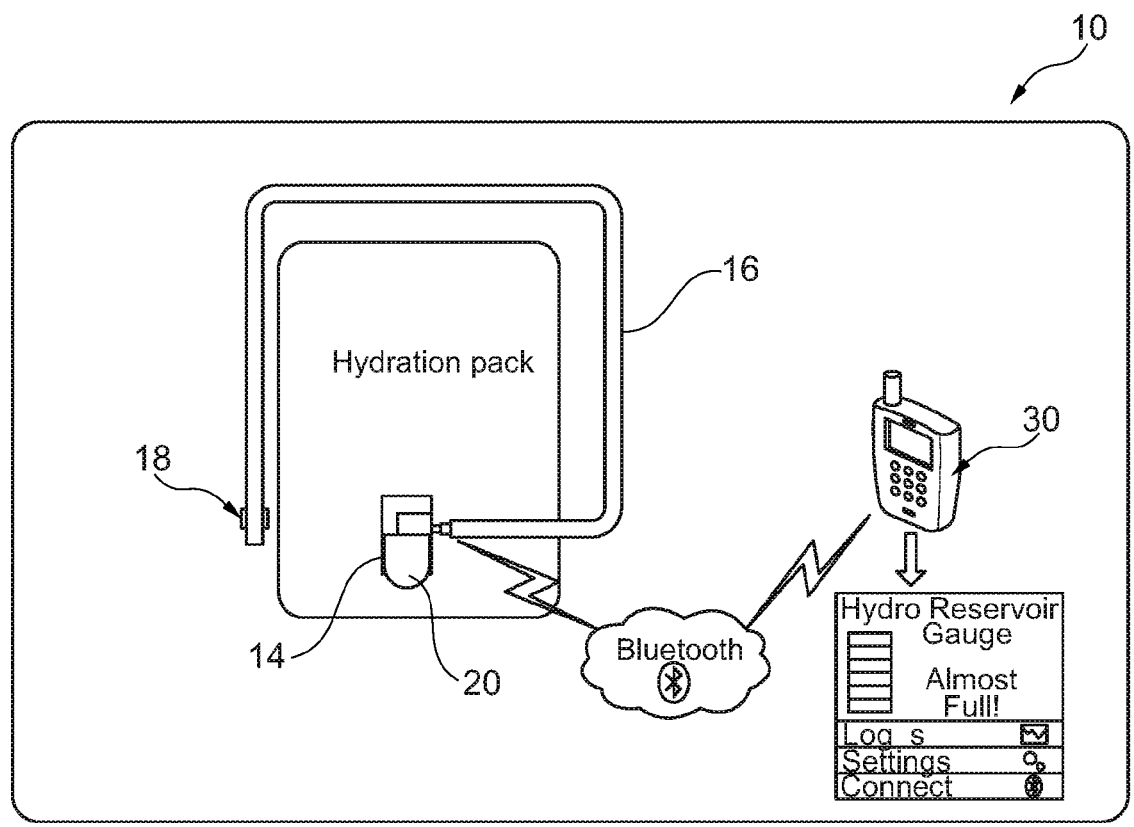
FIG. 1 is a schematic diagram of a preferred embodiment of hydration unit monitoring system.

Referring now to FIG. 1, this shows in schematic form a preferred hydration pack monitoring system 10. The system 10 attaches to a hydration unit 12, which may be a flexible pouch or bag, typically designed to be kept within a rucksack or the like on the user's back. The hydration unit 12 includes an outlet 14 positioned at or close to its base. A feed tube 16, of conventional form, connects to the hydration pack 12 and is typically provided with a mouthpiece 18, again of conventional form and which may or may not have a valve for preventing inadvertent spillage of fluid from the hydration pack 12.

The system 10 includes a monitoring unit 20 which attaches to the outlet 14 of the hydration pack 12. The system 10 also includes a controller which in the example shown in FIG. 1 may be a smartphone 30 which includes an application (or a program) which communicates with the monitoring unit 20 and calculates the amount of fluid within the hydration pack 12 and, preferably, also fluid consumption by the user. The controlled unit 30 preferably communicates with the monitoring unit 20 by means of Bluetooth, in which case both the monitoring unit 20 and the control unit 30 are provided with Bluetooth transceivers. In other embodiments, the controller is built into the monitoring unit 20 such that volume estimates are determined in the unit 20, with the mobile telephone acting solely as a user interface.

Figure 2:
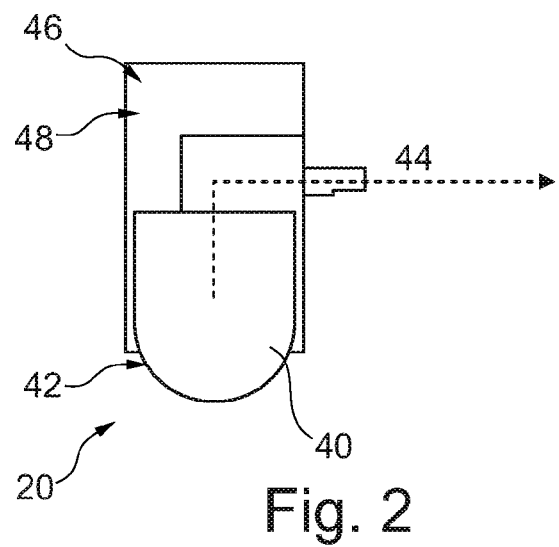
FIG. 2 is a schematic diagram of the preferred embodiment of monitoring unit taught herein.
Figure 3:
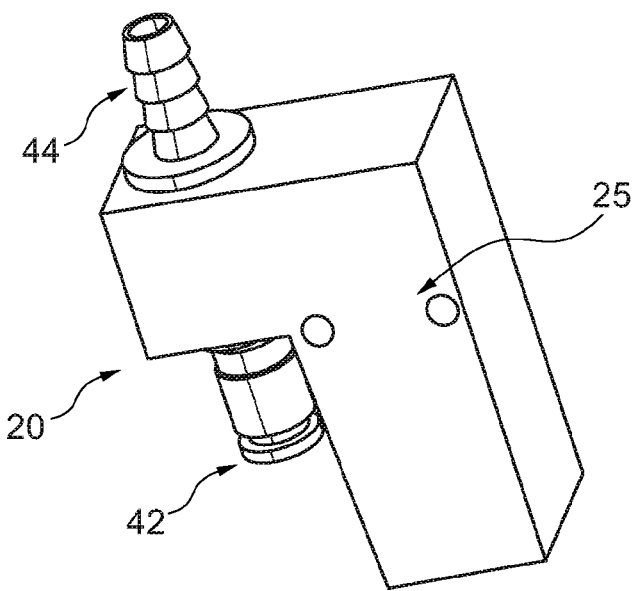
FIGS. 3 to 6 show a practical example of a hydration monitoring system.
Figure 4:
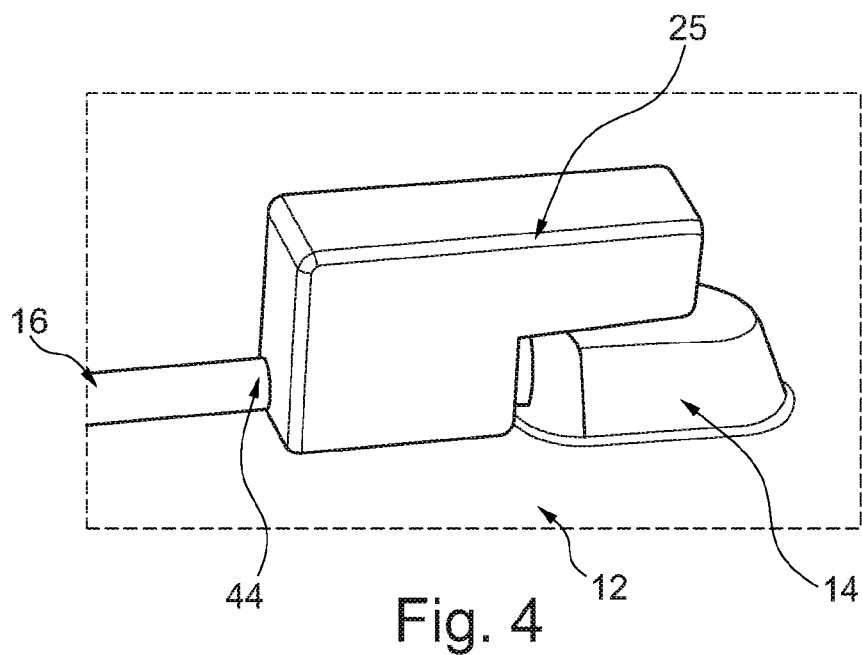

Referring now to FIG. 2, this shows in better detail an embodiment of the monitoring unit 20. The unit 20 includes a chamber 40 into which fluid can pass and an inlet port 42 designed to be coupled to the outlet 14 of the hydration pack 12. An outlet port 44 is also coupled to the chamber 40 and is preferably of a size and design that it can fit readily to conventional feed tubes 16, although it may be provided with its own dedicated feed tube. The monitoring unit 20 includes a pressure sensor 46 which is able to sense pressure within the chamber 40. There is also provided an electronics unit 48, which includes at least a Bluetooth transponder and in some embodiments also a controller for determining an indication of volume of fluid within the hydration pack based on pressure measured by the pressure sensor. The electronics unit 48 also includes, in the preferred embodiment, an accelerometer (not shown in FIG. 2) for obtaining an indication of tilt of the monitoring unit 20, used for calibrating the pressure 10 measurements as described in further detail below. In other embodiments, a tilt sensor of any suitable form may be used in place of an accelerometer.

At the reverse side of the monitoring unit 20 there is preferably provided a fixation element, which may be adhesive pad, for instance, such that the unit 20 can be fixed to the hydration pack 12, to keep the unit 20 stably in place and also to provide reliable tilt measurements. The fixation element may allow for removal of the monitoring unit 20, for example to allow for the hydration pack 12 to be cleaned after usage. Other forms of fixation may be used, including and in some embodiments the coupling to the outlet of the hydration pack may provide sufficient hold to ensure that the monitoring unit 20 is firmly attached to the hydration pack and tilts therewith.

A valve may be provided at the outlet port 44 of the monitoring unit 20 for preventing back pressure from the feed tube 16. This can be particularly advantageous in cases where there is no drinking valve at the end of the feed tube. In many cases, however, a drinking valve is fitted at the distal end of the feed tube, in which case the drinking valve will stop any back pressure being produced, so a monitoring unit valve is not required.

Referring to FIGS. 3 to 6, these show a practical embodiment of the monitoring unit 20 of FIGS. 1 and 2. The monitoring unit includes a housing 25 which is usefully shaped to fit over an outlet element 14 of a hydration pack 12 and includes a recessed side into which the outlet element can fit snugly. In practice, the housing 25 is preferably given an ergonomic shape, FIGS. 3 to 6 depicting a prototype.

The inlet port 42 includes a nozzle or tubular element which is shaped and sized to fit into the outlet of the hydration pack 12 with a watertight seal. The inlet port 42 may be provided with one or more suitable O-ring seals to ensure a water tight connection with the hydration pack. The unit 20 may in some embodiments include a one or more different fittings or attachments to accommodate hydration packs having different shapes or designs of outlet.

The outlet port 44 of the unit 20 has, in this example, a series of outwardly tapering annular ridges to hold a feed tube 16 in place. It will be appreciated that other fittings may be used. In some embodiments, one or more O-ring seals may be provided at the outlet port 44 for sealing purposes.

The inlet and outlet ports 42, 44 are usefully arranged linearly, which enables the feed tube 16 to maintain the same orientation as it would if attached directly to the outlet fitting of the hydration pack 12.

Figure 5:
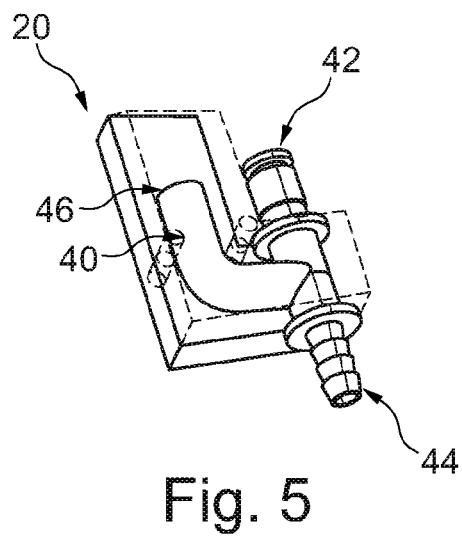
Figure 6:
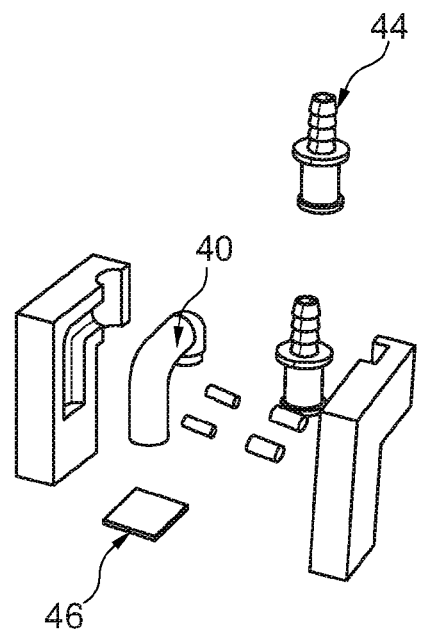

With reference particularly to FIGS. 5 and 6, in this example the chamber 40 is formed by a curved tubular member which resides in the housing 25 and in practice extends downwardly, towards the hydration pack outlet. At the end of the tube there is fitted the pressure sensor 46 and the control unit 48. The pressure sensor 46 may provide or be disposed in a fluid tight seal at the end of the tubular chamber 40.

The inlet and outlet ports 42, 44 need not have the shapes shown and may differ in other embodiments. The inlet port 42 could also be in the form of a replaceable adaptor to fit to different designs of hydration pack. If need be, a connection hose may be provided for coupling between the inlet port 42 and the outlet 14 of a hydration pack.

The unit 20 shown in FIGS. 3 to 6 may be designed to lie flatter to the hydration pack 12, for example by rotating the tubular chamber 40 by 90 degrees to one side, which will allow the design of a shallower housing.

Referring now to FIGS. 7 to 11, these show another practical embodiment of monitoring unit 20, in particular a more ergonomically shaped housing. As with the embodiments of FIGS. 2 to 6, monitoring unit 20 includes a housing 25, an inlet port 42 and an outlet port 44.

Figure 7:
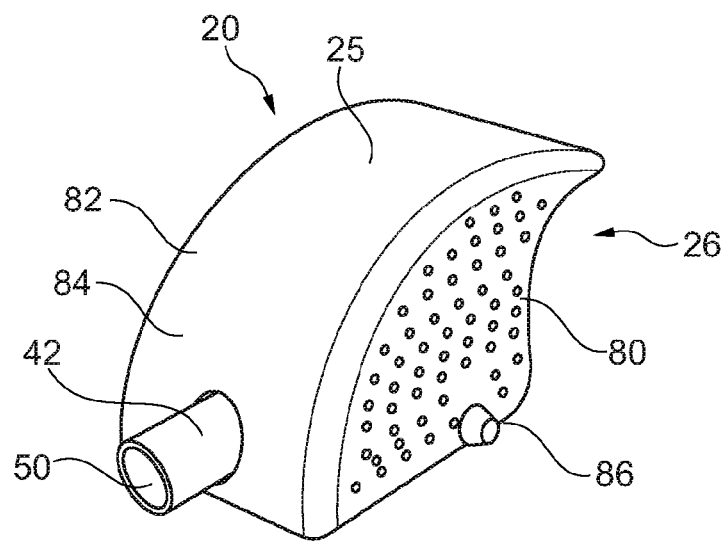
FIGS. 7 to 11 show a further practical example of a hydration monitoring system.

Referring to FIG. 7, this shows a bottom perspective view of monitoring unit 20 including housing 25 with a convex side 84 and a recessed side 26 and two side walls 80, 82. As described above, recessed side 26 allows the outlet element to locate snugly within the perimeter of housing 25. Inlet port 42 protrudes from the convex side 84 and includes a first tubular element 50. The tubular element 50 includes an internal diameter equal to or smaller than the outer diameter of a standard hydration bladder nozzle and is made of resilient material so that it can fit tightly over the hydration bladder nozzle, resulting in a water-tight connection between the monitoring unit 20 and the hydration pack 12. In some embodiments, tubular element 50 is made of same or similar material, and of equivalent dimensions, to a conventional feed tube. Side walls 80, 82 of housing 25 include dimples to aid gripping of the monitoring unit 20 by a user.

A pin 86 is provided protruding out from side wall 80. Pin 86 provides a plug (not visible) that inserts into housing 25 and blocks the entry to a battery compartment within monitoring unit 20. Preferably, pin 86 provides a water-tight seal to the battery compartment. Removing pin 86 from housing 25 provides access to the battery compartment.

Figure 8:
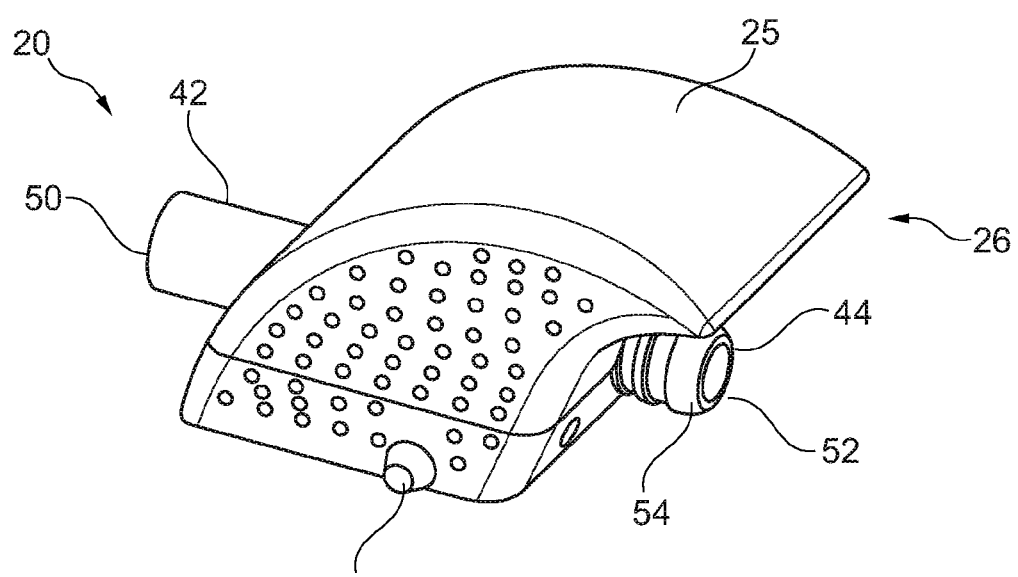

FIG. 8 shows a side perspective view of monitoring unit 20. A second tubular coupling 52 can be seen protruding out from the recessed side 26 and opposite first tubular element 50. Tubular coupling 52 has an outer diameter sized such that it can fit tightly within a standard feed tube and provide a water-tight connection between the monitoring unit 20 and the feed tube. In some embodiments, the tubular coupling 52 includes one or more circumferential ribs 54 of wider outer diameter to provide a tight fit within the feed tube. This can be most clearly seen in the side view shown in FIG. 9. Additional circumferential ribs 56 may be provided along tubular coupling 52 to help hold the feed tube in place.

The second tubular coupling 52 is made of more rigid material than the first tubular element 50, such that it may be grasped and the end inserted into a feed tube.

Figure 9:
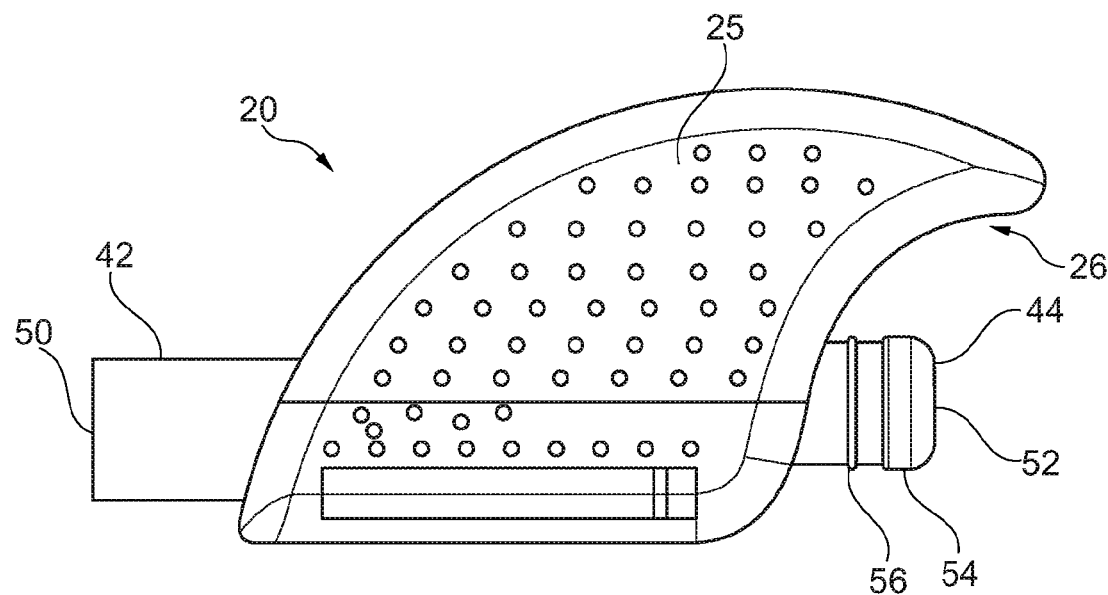

As can be seen in FIG. 9, the first tubular element 50 and the second tubular coupling 52 are arranged along a common axis, which enables the feed tube to extend from the hydration pack just as it would have done when fitted directly thereto. Thus, the ergonomics of the original assembly without the monitor are maintained.

Figure 10:
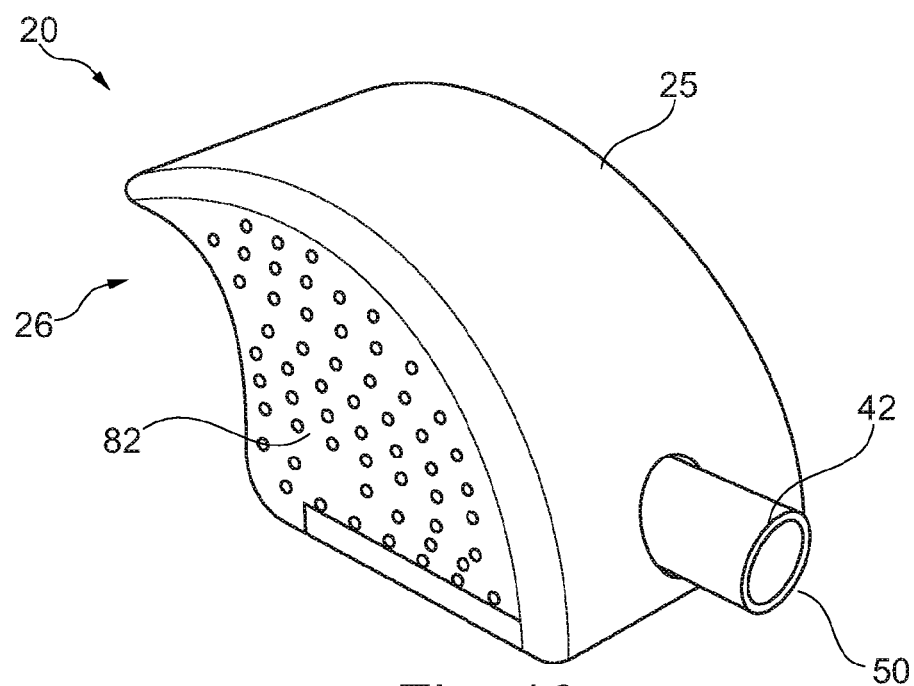
Figure 11:
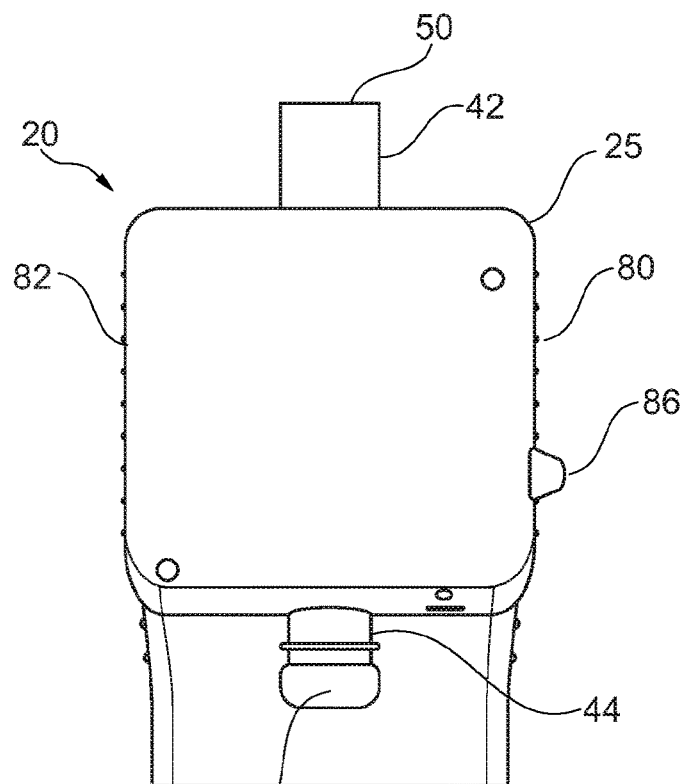

FIG. 10 shows the monitoring unit 20 from a top perspective view while FIG. 11 shows the monitoring unit 20 from a rear perspective view.

Figure 12:
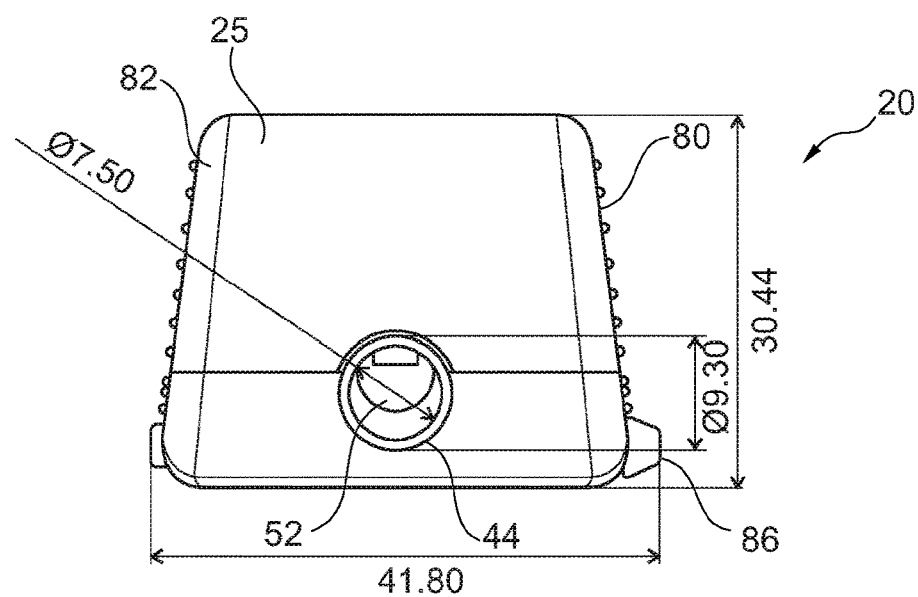
FIGS. 12 to 14 show example dimensions of the hydration monitoring system of FIGS. 7 to 11.
Figure 13:
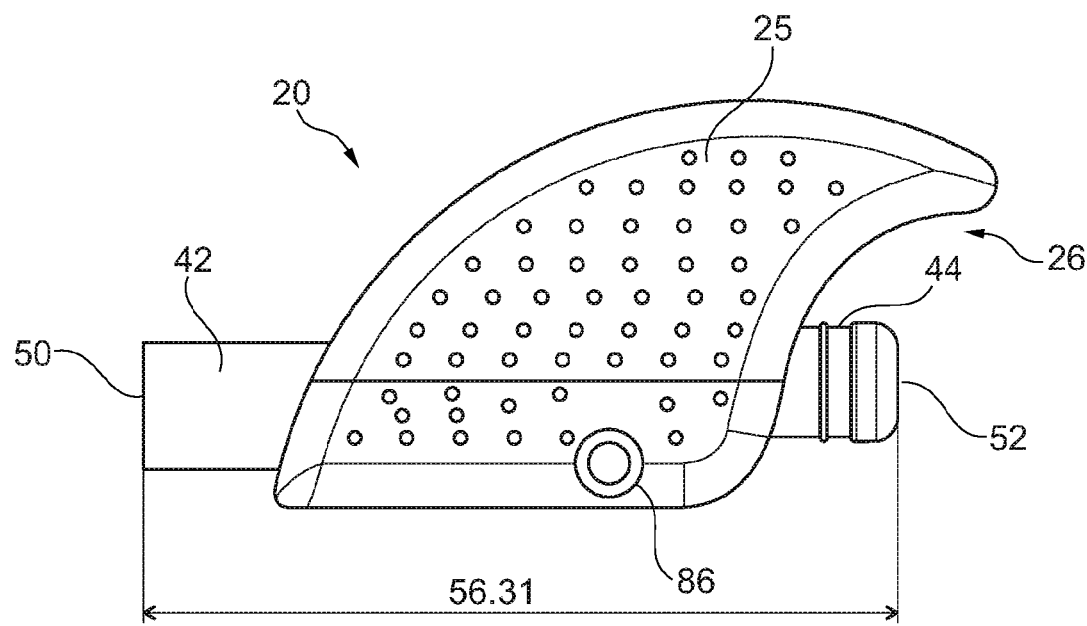
Figure 14:
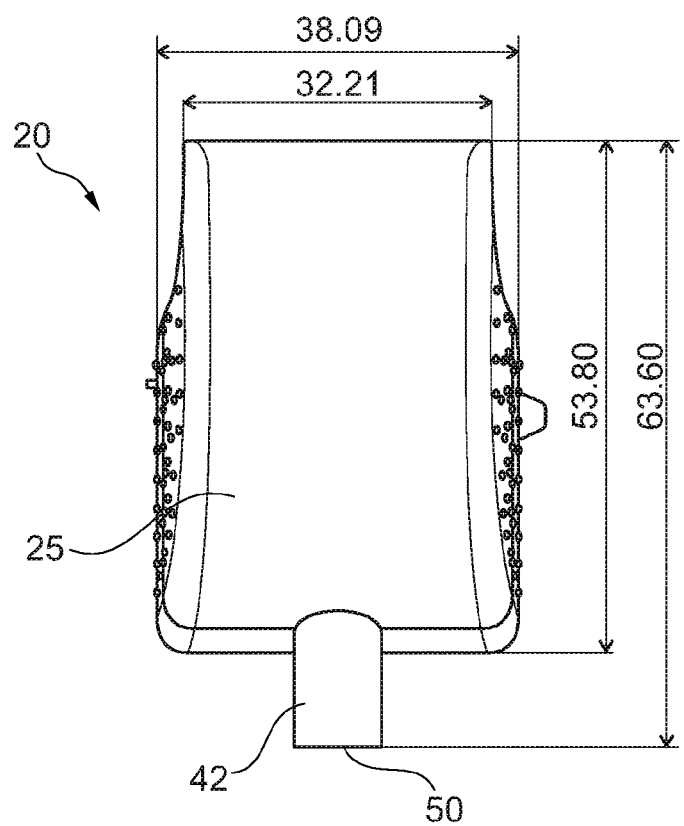

FIGS. 12 to 14 show example dimensions for the monitoring unit 20.

Figure 15:
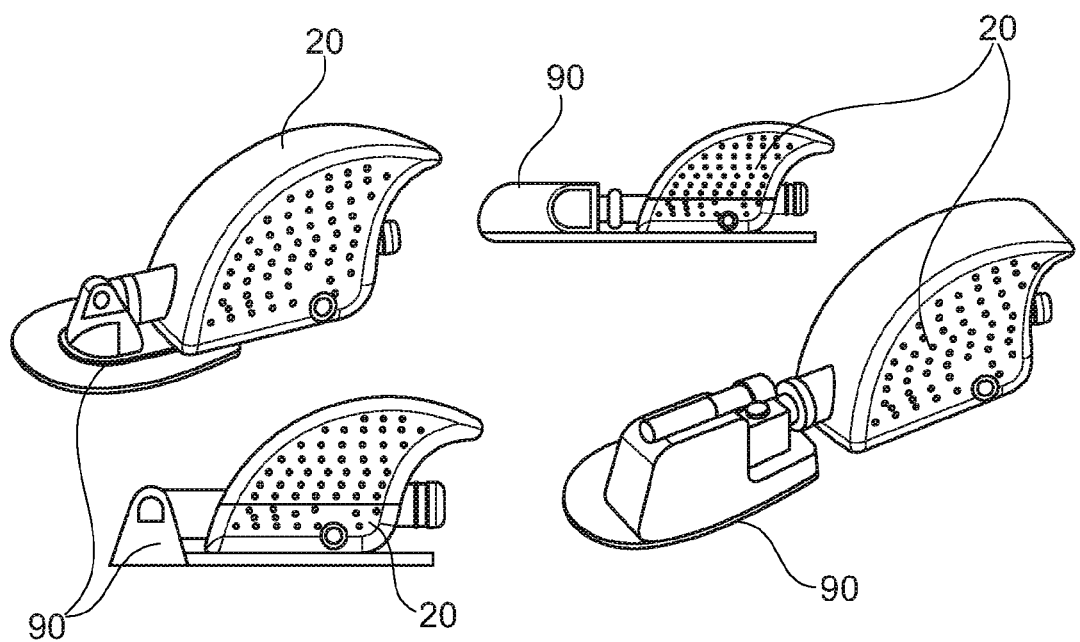
FIG. 15 shows the hydration monitoring system connected to various designs of outlet nozzle or adaptor for hydrations packs.

FIG. 15 shows monitoring unit 20 connected to various designs of outlet nozzle or adaptor 90 of different hydration packs. For the sake of clarity of the Figures, the hydration packs are not shown in these Figures. The inlet tube 42 from the monitoring unit 20 fits into the outlet nozzle for the hydration packs 12, and is able to accommodate the different shapes and designs of outlet. In practice, the use of a tube as the connector from the monitoring unit 20 to the outlet of a hydration pack avoids the need to have different connectors for different hydration packs. The feed tube is typically a standard component in the industry; that is, the majority of hydration packs use a common size of feed tube. As a result, using a connector in the form of a tube provides a very efficient coupling arrangement and one which is compatible with the vast majority of existing products.

Figure 16:
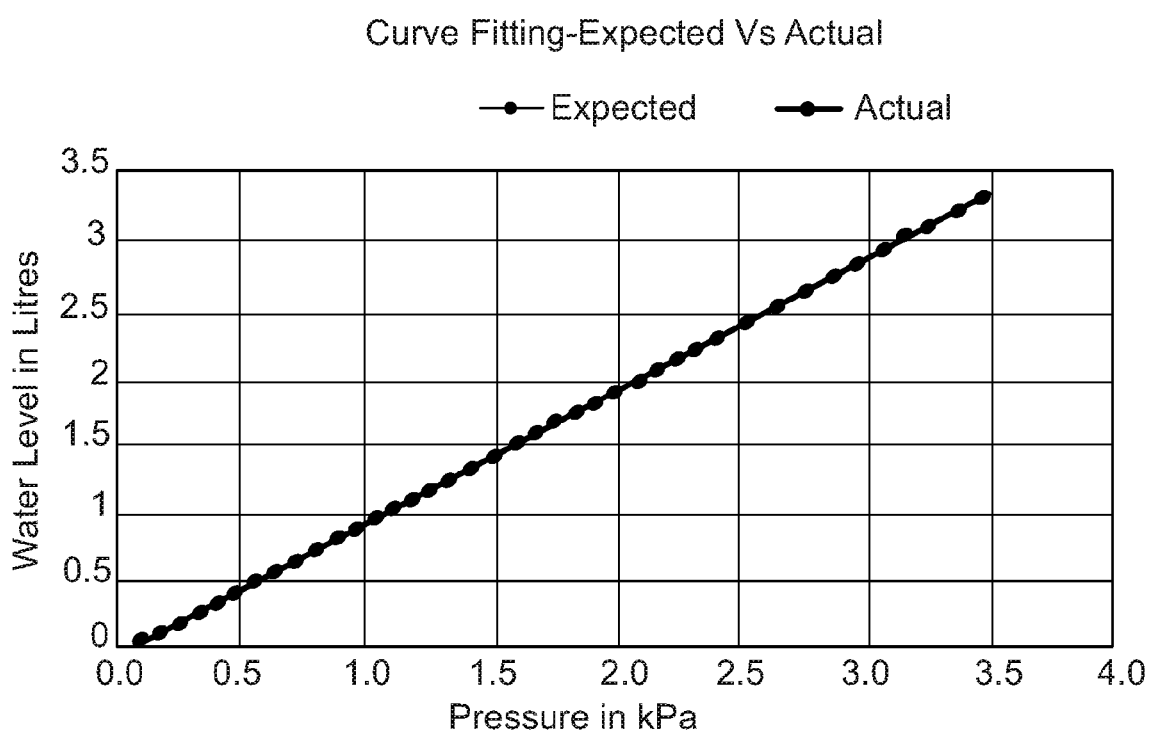
FIG. 16 is a curve of expected volume indication provided by the system and actual volume in the hydration unit.

In practical tests, as can be seen in FIG. 16, the system of FIGS. 1 to 15 can provide an accurate indication of volume of liquid in a hydration pack 12, with the estimated volume being a close match to the actual measured volume. This is the case when the hydration pack 12 is disposed vertically or substantially vertically.

Figure 17:
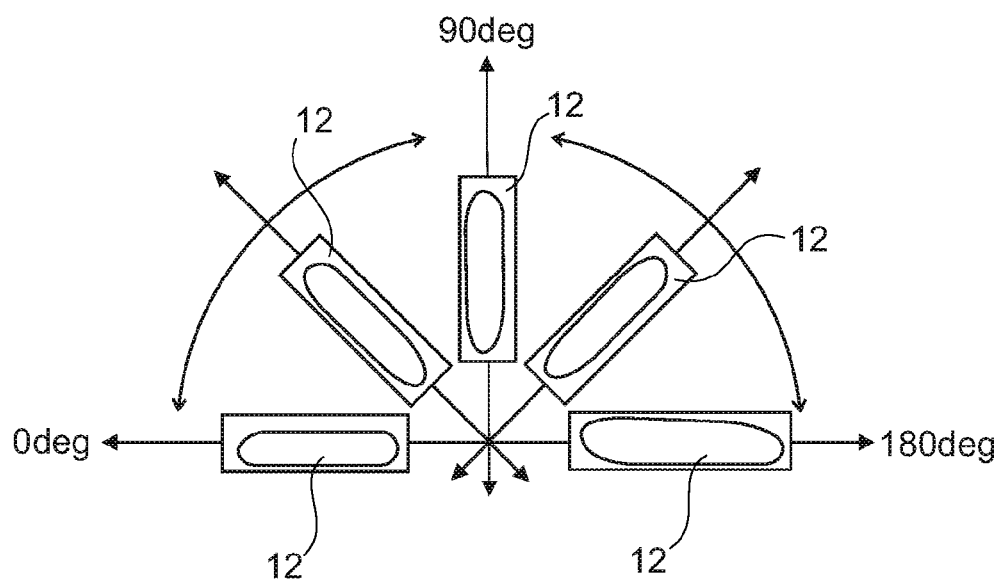
FIG. 17 is a schematic diagram of a hydration pack in various orientations in which it might be held.

However, as depicted in FIG. 17, the hydration pack 12 could be held in a variety of different orientations in use, typically from around 0 to around 180° at most. This may, for instance, be as a result of the manner in which a user chases to carry the hydration pack, the user's orientation during sport or exercising, and so on. For example, when the hydration pack 12 is held in a rucksack by a runner or walker, it is likely to be kept substantially vertically, whereas when the user is cycling, the pack 12 may be close to horizontal.

Figure 18:
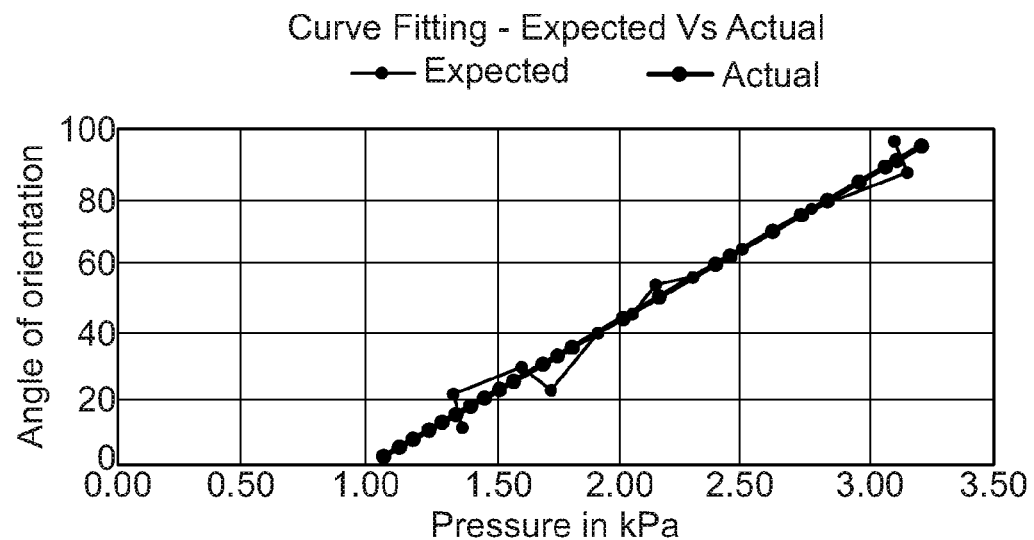
FIG. 18 is a graph of expected volume indication provided by the system and actual volume in the hydration unit when the hydration pack is tilted at angles of 0 to 90 degrees when filled with three liters of water.

Referring now to FIG. 18, for a hydration pack filled with three liters of water it can be seen how the expected volume estimate derived from a pressure measurement alone deviates with angle of orientation of the hydration pack 12. In this particular instance there is reasonable correlation between the expected, estimated, volume based on pressure measurements alone and actual volume within the hydration pack 12 at relatively low angles of tilt.

Figure 19:
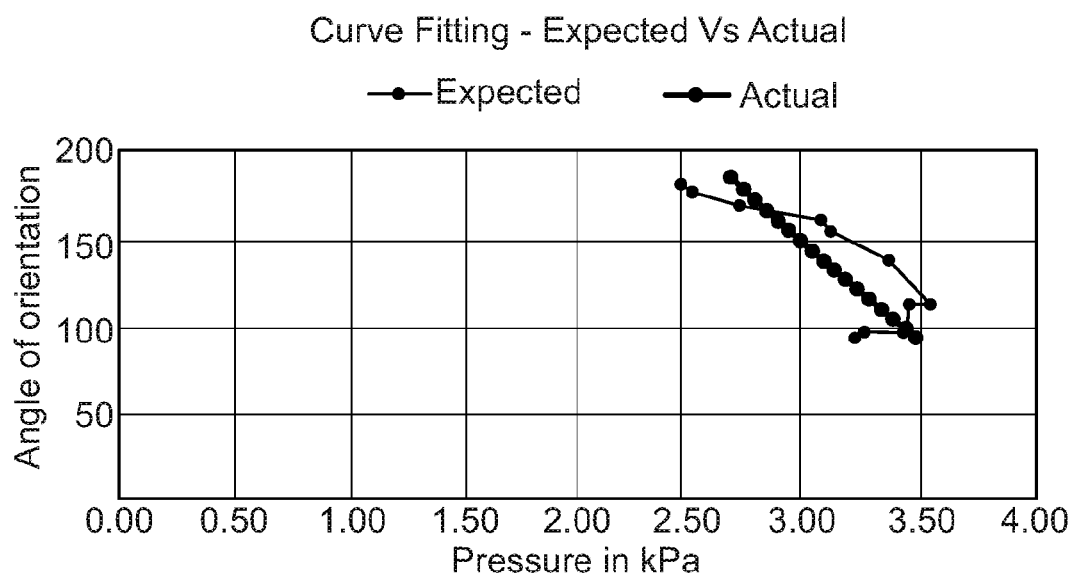
FIG. 19 is a graph of expected volume indication provided by the system and actual volume in the hydration unit when the hydration pack is tilted at angles of 90 to 180 degrees when filled with three liters of water.
Figure 20:
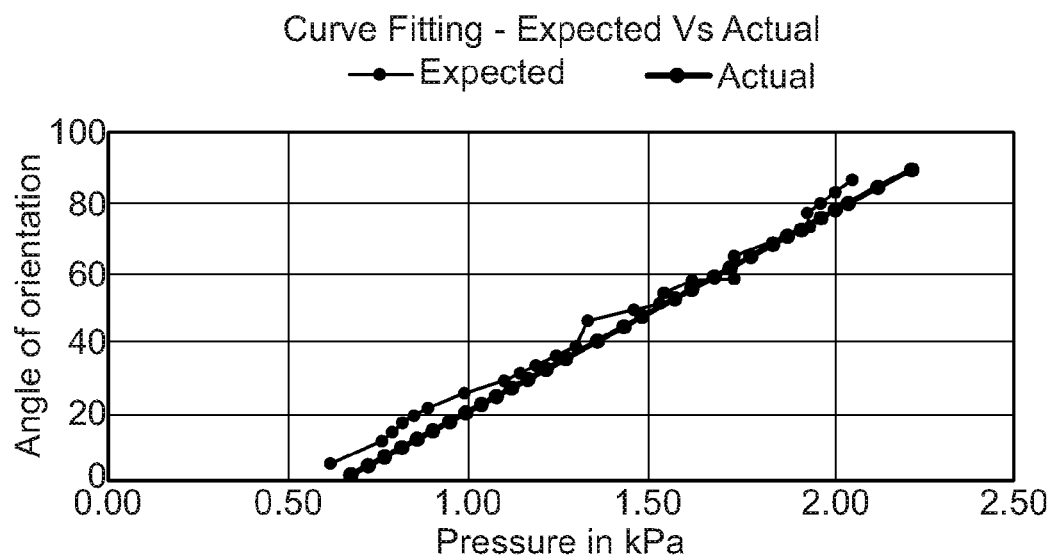
FIG. 20 is a graph of expected volume indication provided by the system and actual volume in the hydration unit when the hydration pack is tilted at angles of 0 to 90 degrees when filled with two liters of water.
Figure 21:
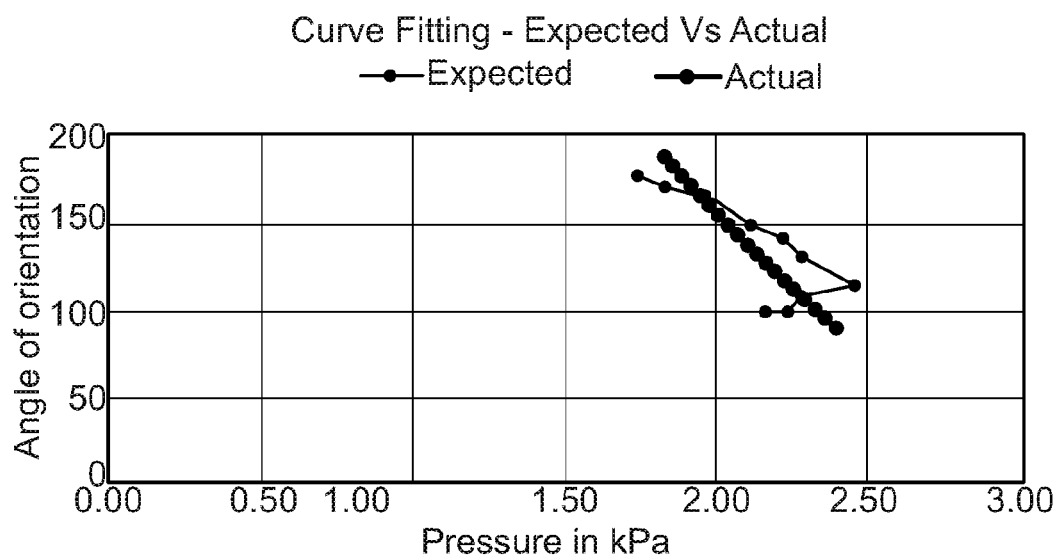
FIG. 21 is a graph of expected volume indication provided by the system and actual volume in the hydration unit when the hydration pack is tilted at angles of 90 to 180 degrees when filled with two liters of water.

FIG. 19 shows the same hydration pack, filled with three liters of water, when tilted at angles from around 200° to less than 100°. It can be seen in this instance that there is a greater deviation between the expected, estimated, water volume based on pressure measurement alone and the actual volume of liquid in the pack 12. FIG. 20 is similar to FIG. 18, for a hydration pack filled with two liters of water, while FIG. 21 is similar to FIG. 19, for a hydration pack filled with two liters of water.

In general, the lesser the amount of liquid in the pack 12 the greater will be the variations in pressure measurements on tilting of the pack.

The preferred system 20 compensates for deviations in measurements caused by tilt of the hydration pack 12, by usage of the readings from the tilt angle sensor, in the preferred embodiment the accelerometer. In one embodiment, the controller includes a database with correlation values based on pressure and tilt angle, such that pressure measurements can be calibrated on the basis of the detected tilt angle and the expected deviations caused by the tilt taken into account as appropriate in the calculation of remaining liquid. The database preferably also includes calibration tables for different liquid volumes in order to take into account variations caused by the amount of liquid in the pack, and may also include tables for different types of hydration pack, and so on. In other embodiments, in place of a look-up table in a database, the controller may include a calibration algorithm.

It is envisaged that the preferred system may provide an algorithm giving the user with the ability to self-calibrate the system, which will enable the user to choose a preferred hydration pack and calibrate the monitoring unit to suit that pack. The controller may also be configured to provide a calibration routine to allow for calibration of the accelerometer reading, in order to account for the monitoring unit to be attached by the user to the user's hydration pack in orientations other than directly aligned with the main body of the pack. This self-calibration routine may be done within the application in a mobile telephone or within a dedicated controller.

The pressure sensor may also be calibrated, in one example by fitting the monitoring unit 20 to the user's hydration pack and then filling the hydration pack to predetermined levels, preferably to maximum capacity and then to at least one other known liquid level, such as minimum level or any intermediate level indicated on the hydration pack. The pressures detected by the pressure sensor 46 can then be calibrated to the known liquid amounts, preferably by curve fitting in order to generate calibration coefficient values for estimating accurately the amount of liquid in the pack at intermediate pressures. Again, pressure calibration can be performed within a mobile telephone application or a dedicated controller.

Figure 22:
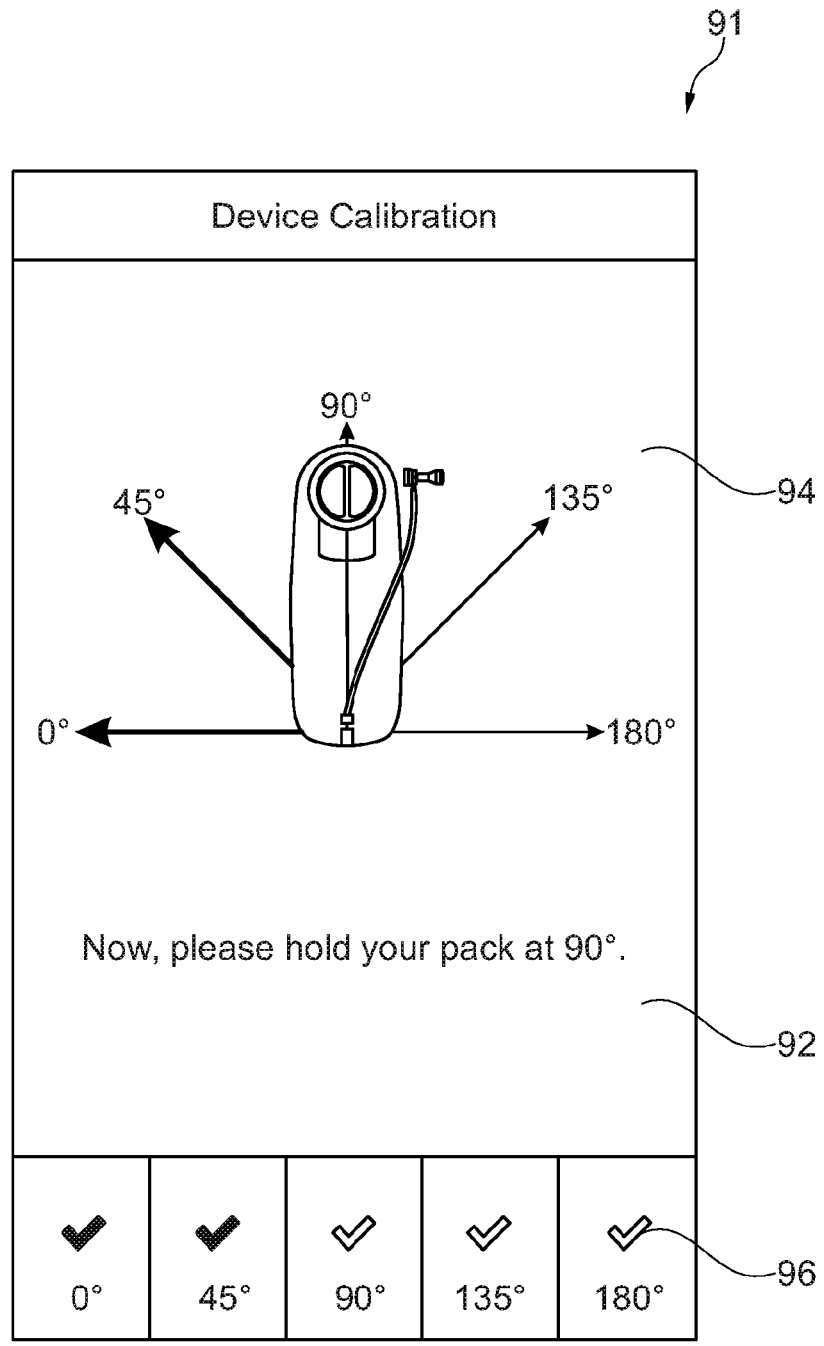
FIG. 22 shows a practical example of a device calibration screen.

FIG. 22 shows an example of a calibration screen 91 within an application used by a user when calibrating the system. Instructions 92 on the calibration screen indicate to a user the angles the hydration pack needs to be tilted at, to allow the pressure sensor 46 to calibrate at the known angles. For complete calibration, the tilt angle ranges from 0° to 180°. An image of the hydration pack 94 tilted at various angles may be provided to help guide the user. The calibration screen 90 may also include a check box or tick section 96 where a tick appears against each angle once calibration for that angle is complete. In use, during a calibration routine a user is taken through the various steps to tilt the bladder to the set angles, and the controller obtains a measure of pressure variation caused by the tilt. This allows the system to work with different design, shapes and sizes of hydration pack.

Figure 23:
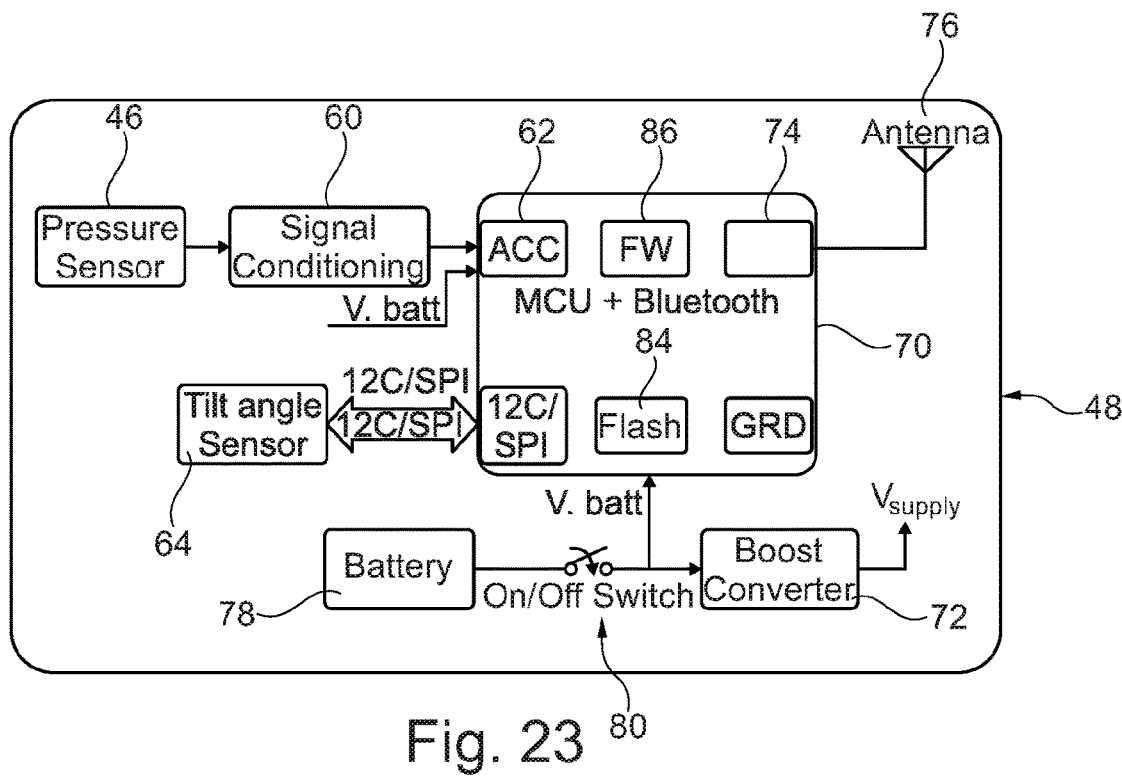
FIG. 23 is a schematic diagram of the preferred embodiment of system components.

FIG. 23 shows in further detail the components of the preferred embodiment electronic module 48 of FIG. 2. The pressure sensor 46 is disposed so as to measure fluid pressure at the outlet 14 of the pack 12. Signal conditioning circuitry 60 may be included for scaling the pressure sensor analogue voltage (differential voltage) to match with the analogue to digital converter (ADC) 62 of microcontroller 70. The controller 70 is preferably also configured to power down the pressure sensor 46 when unused.

The tilt sensor (accelerometer) 64 is used to identify the orientation/tilt angle of the pack 12. In a practical embodiment, the tilt sensor 64 is interfaced to the controller via an I2C/SPI protocol as an interface. The X, Y and Z axes acceleration values are then obtained from the tilt sensor 64 to identify the pack's orientation. This module 64 is preferably also put in a power down mode when unused.

Power is preferably derived from a 3V coin cell 78, connected via an ON/OFF switch 80. The ON/OFF switch 80 is preferably readily accessible to the user to turn off the device when not used and to turn it on as necessary. A boost converter 72 may be provided to power the pressure sensor 46 (when the latter requires a higher operating voltage) from the coin cell. This module 72 is preferably also put in power down mode when unused. The coin cell voltage can be monitored by the ADC 62 of microcontroller 70 to alert the user in the case of low battery voltage.

The controller 70 also includes a Bluetooth transceiver 74 connected to an antenna 76, flash memory 84 and RAM 86 for storing controller algorithms (firmware) and, in some embodiments, calibration data. The Bluetooth transceiver 74 will typically transfer measurement readings to the user's telephone.

Figure 24:
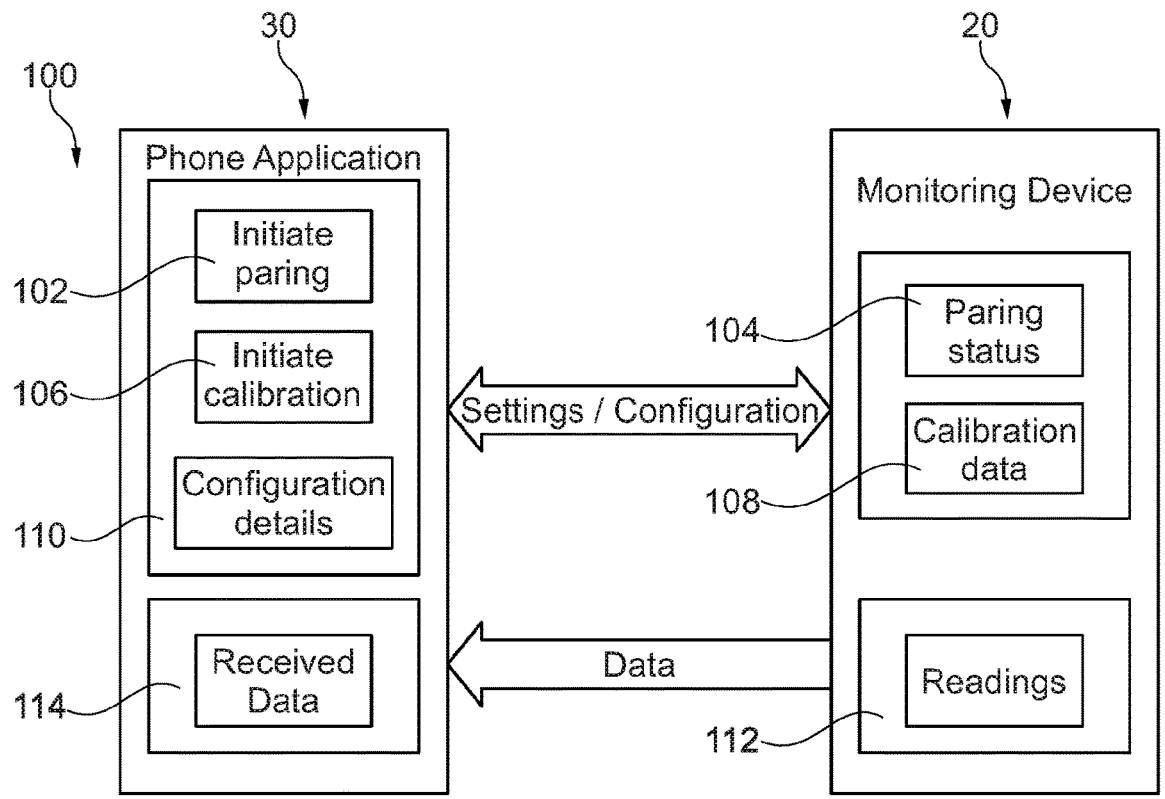
FIG. 24 is a schematic diagram of the preferred wireless protocol between the monitoring unit and the user interface.

Referring now to FIG. 24, this shows in schematic form the communication set up between the monitoring device 20 attached to the hydration pack 12 and the remote controller, in this embodiment an application on a smartphone 30. At a first step, the application 30 carries out, at step 102, a pairing routine in order to pair the smartphone 30 to the monitoring device 20. When this is completed successfully, a suitable flag is set at step 104 in the monitoring device (typically in memory of the controller 70 of the electronic system of FIG. 13). The preferred application then initializes a calibration routine in step 106, providing guidance to the user as to how to fill the hydration pack and how to orient the hydration pack to obtain the required calibration data. At step 108 the controller 70 generates calibration data which is then transferred back to the application 30 to generate a set of configuration details at step 110, in effect to calibrate the determination of the remaining volume of fluid within the hydration pack 12 using graphs similar to those shown in FIGS. 16 and 19 to 22. This data can be specific to the user's hydration pack. The system may be calibrated only when the monitoring unit 20 is first fitted to a hydration pack 12 or refitted to an existing hydration pack 12.

When the configuration details have been determined (step 110), the system proceeds to what could be described as running operation, with readings periodically taken by the monitoring unit, at step 1 12, and then transferred to the application 30, at step 114, for processing and displaying on a display of the smartphone 30 an indication of the amount of liquid remaining in the hydration pack 12. In the preferred embodiment, the application 30 also provides an indication of fluid consumption to the user, determined by obtaining a measure of the rate of reduction in measured liquid in the hydration pack 12 over specific time periods. This can in some embodiments be correlated to the user's desired rate of consumption of fluid or to predetermined criteria, either built into the application 30, typically dependent on the type of exercise being performed, or pre-programmed into the application 30 by the user, for example.

Figure 25:
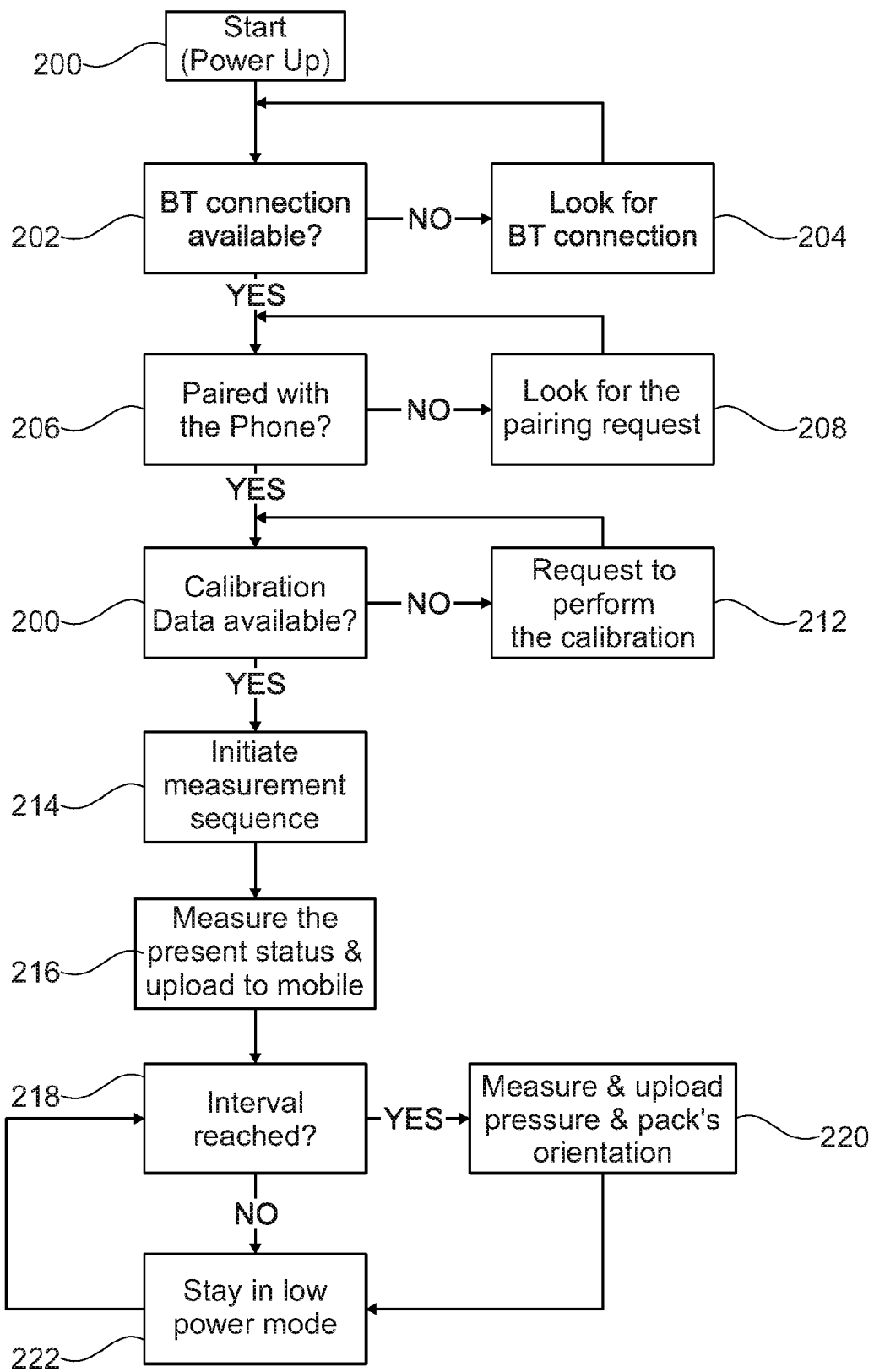
FIGS. 25 and 26 are flow charts showing the operation of the system of the preferred embodiment.

Referring now to FIG. 25, this shows the routine performed by the monitoring unit 20. At step 200, the monitoring unit is powered up, for example by the user pressing or toggling the on/off switch 80 or by detection of movement of the pack, for example by the accelerometer 64. Once powered up, the routine proceeds to step 202 in which it determines whether a Bluetooth connection has been detected. If this is not the case, the routine passes to step 204 at which the controller 70 continues looking for a Bluetooth connection. When a Bluetooth connection has been found, at step 206 it is determined whether the monitoring unit 20 has already been paired to the phone 30 and if this is not the case, at step 208 the routine looks for a pairing request from the telephone 30. Once paired, the routine passes to step 210 to determine whether calibration data is available. If this is not the case the controller 70 sends, at step 212, a request to perform calibration. The routine then passes to step 214 to initiate a measurement sequence and in the first step, that is step 216, the controller 70 obtains a measure of the current status of the monitoring device 20 and transmits that to the mobile telephone 30. At step 218, the controller 70 determines whether a pre-determined time interval has been reached and when this is the case it passes to step 220 to take a measure of pressure and orientation, which is forwarded to the telephone 30 via the transceiver 7 4. The routine then passes to step 222, which is reached also if the pre-determined time interval has not elapsed, at which the monitoring unit 20 is kept in a low power mode until the pre-determined interval has been reached. In practice, it is preferred that measures of pressure and orientation are taken no more than once every 60 seconds in order to conserve battery charge. This interval can, of course, be changed in dependence upon the expected or desired consumption of fluid and this could be user-adjustable in some embodiments.

Figure 26:
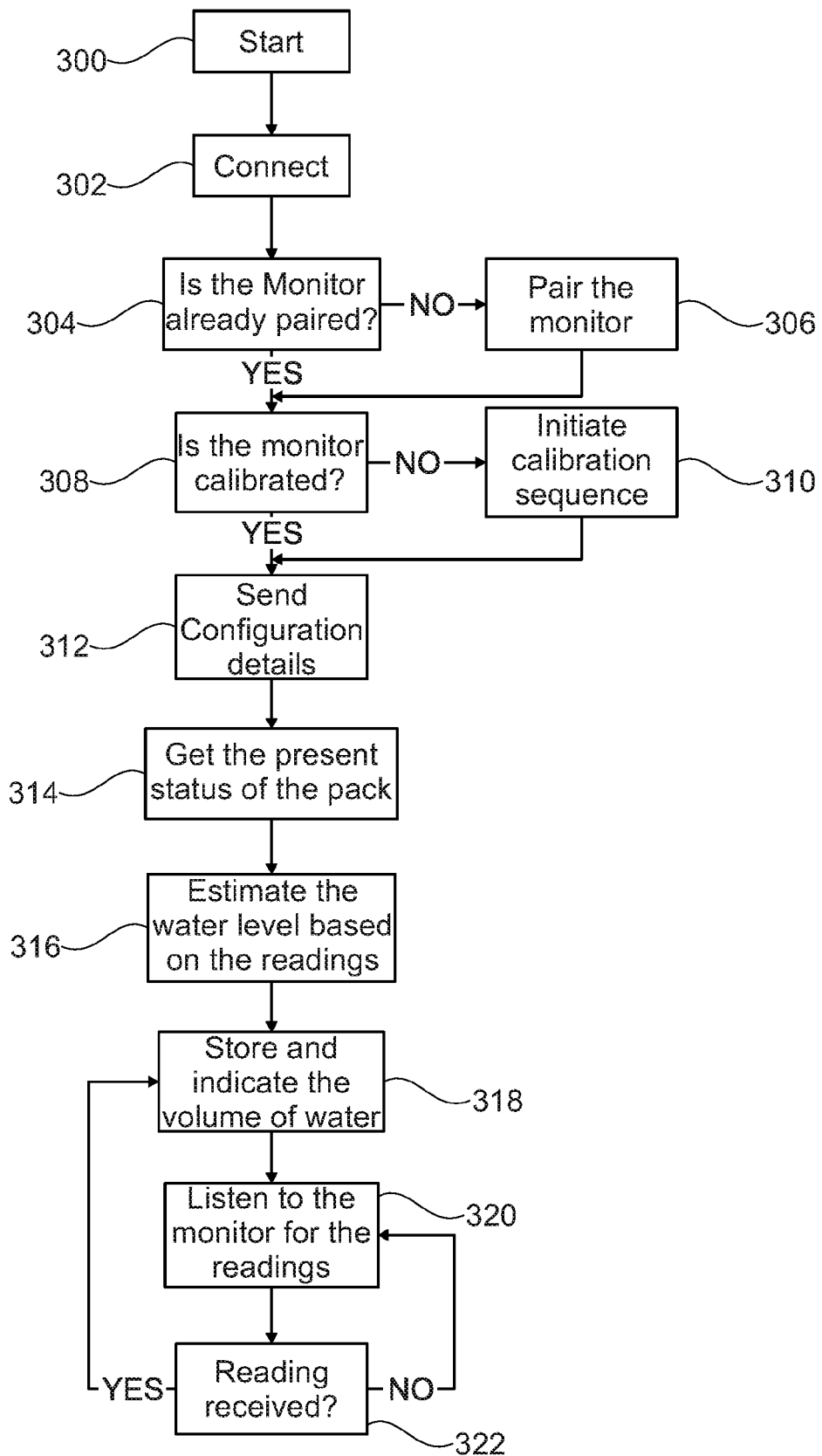

Referring now to FIG. 26, this shows a routine performed by the application of the mobile telephone 30 in monitoring and advising on the status of the hydration pack 12. The routine starts at step 300, typically on starting up of the powering up of the application. At step 302 a connect sub-routine is initiated, which, at step 304, it is determined whether the monitoring unit 20 is already paired to the telephone 30. If this is not the case, at step 304, the routine pairs the telephone 30 to the monitoring unit 20. Once paired, the routine passes to step 308 at which it is determined if the monitoring unit 20 has been calibrated and if this is not the case, the routine passes to step 310 at which a calibration sequence is initiated. Once calibrated, the routine continues to step 312 at which configuration details are sent to the monitoring unit 20 to be stored in memory of the controller 70. At step 314 the routine obtains the current status of the hydration pack 12 from the monitoring unit 20 and at step 316 the application estimates the amount of liquid contained in the hydration pack 12 on the basis of the status readings obtained in step 314. At step 318 the routine stores the estimated volume of water and provides an indication of this to the user, for example as a graphical and/or numerical indicator on the display of the telephone 30. At step 320, the routine listens out for further transmitted readings from the monitoring unit 20. When it is detected at step 322 that new readings have been received, the routine passes back to step 318; otherwise it returns to step 320 to continue listening for the receipt of new readings. When the routine passes back to step 318, the application 30 will store the new readings and provide a new indication of the volume of water remaining in the hydration pack 12 and, in some embodiments, to generate an indication of rate of liquid consumption. This may be indicated visually by means of a vertical bar graph with colored or illuminated bars changing from top down as the level of liquid in the hydration pack 12 reduces. Advantageously, the bar graph is designed to give a visual indication representative of the level of remaining fluid. In an embodiment, the volume of the water left within the hydration pack is represented in the form of six or more vertically stacked bars, each representing 16.6% of total pack capacity.

There may also be displayed a numerical indication of remaining liquid, for example as a percentage or volume. Indications of consumption may be as volume of liquid drunk over time, or may in some embodiments be in the form of, for example, colored indications or other graphical indications representative of adequate, excessive or insufficient rate of consumption of liquid during a period of exercise.

Preferably, the display of the telephone 30 continues to display the last determined water level until the next reading is received.

In a practical embodiment, the default measurement and upload interval is chosen to be 60 seconds. If a user wishes, this value can be increased or reduced as desired from the telephone application. It will be appreciated that more frequent readings will reduce battery life.

In some embodiments, measurements taken during the consumption of liquid will be discarded as they will not give estimates of the volume of the liquid left within the pack. More specifically, as the user draws liquid through the feed tube 18, by sucking on the mouthpiece 18, the pressure in the chamber of the outlet device 40 will drop and therefore no longer provide a reliable indication of the volume of fluid remaining in the hydration pack 12. Drinking by the user can be determined by a sudden change in measured pressure or, where provided, by means of an electronic backflow valve at the outer port 44 of the monitoring unit 20. Such a valve would include an indicator of the status of the valve (open or closed), with an open status indicating that the user is drinking fluid. Such a valve could be opened by differential pressure between the chamber of the outlet device 40 and the feed tube 16, caused by the user sucking on the mouthpiece 18, or be electronically controlled. The valve will close once the user stops drinking.

In a practical embodiment, the remote device 30 need not store historical readings for cases where the user is interested only in real-time or instant values. However, in other embodiments, the mobile phone 30 may store historical data, in order to provide the user with an indication of the rate liquid consumption of consumption.

In case that the Bluetooth communication is unavailable, the monitoring device 20 will not continue taking the measurements until the phone communication is restored.

The monitoring device 20 is preferably calibrated with an actual pack used, rather than by a factory based calibration which is not pack specific. This would involve the user filling his/her hydration pack or container with specific amount of water (the telephone application 30 would assist the user) and setting the calibration point values.

In a practical embodiment, the following components may be used, although it is to be understood that these are examples only and that alternatives are also suitable. A Bluetooth module nRF51822 (from Nordic Semiconductor)

is a suitable option. A suitable pressure sensor module is MP3V5010 (from Freescale Semiconductor), which has a pressure range from 0 to 10 kpa. A suitable accelerometer is LIS2DH12TR (from STMicroelectronics).

Advantageously, the monitoring device 20 will use BLE 4.0 for communication with phone. It is preferred that the monitoring device 20 is designed to accommodate a standard ⅜ inch (9.5 mm) feed pipe, making the device easily fitted to existing hydration assemblies.

It is to be appreciated that the teachings herein are no limited to the use of a smart mobile phone for calculating volume, consumption and communicating to the user. Other embodiments may use other devices, such as a watch, any other smart device, a dedicated control and display unit, and so on.

All optional and preferred features and modifications of the described embodiments and dependent claims are usable in all aspects of the invention taught herein. Furthermore, the individual features of the dependent claims, as well as all optional and preferred features and modifications of the described embodiments are combinable and interchangeable with one another.

The invention claimed is:

1. A system for monitoring an amount of fluid in a hydration unit having a fluid outlet, comprising:
   a monitoring unit comprising:
     a fluid chamber;
     an inlet port attachable to a fluid outlet of a hydration unit;
     an outlet port for attachment to a feed tube;
     a pressure sensor mounted to the monitoring unit and in pressure communication with the fluid chamber; and
     a tilt sensor operable to determine an angle of tilt of the hydration unit;
   a controller in use coupled to the pressure sensor and to the tilt sensor, for obtaining a pressure sensor signal therefrom, the controller being operable to determine from the pressure sensor signal an indication of a volume of fluid in the hydration unit, and to calibrate pressure measurements based on the angle of tilt determined;
   a user interface coupled to the controller and operable to provide an indication of the volume of fluid in the hydration unit; and
   a valve for preventing back pressure being introduced into the chamber from a feed tube, wherein the valve is disposed in the monitoring unit and is electronically controlled by the controller.

2. The system of claim 1, wherein the tilt sensor is an accelerometer.

3. The system of claim 1, wherein:
   the controller is mounted to the monitoring unit; and
   the system further comprises a communications unit coupled to the controller and operable to send or receive data between the controller and the user interface.

4. The system of claim 1, wherein the controller comprises a database of calibration values for calibrating the indication of the volume of fluid derived from the pressure sensor signal.

5. The system of claim 1, wherein the controller is operable to obtain a sequence of pressure measurements and to determine therefrom a fluid consumption.

6. The system of claim 1, wherein the user interface is an application or a program for a mobile telephone or a watch.

7. The system of claim 1, wherein the monitoring unit is integral with the hydration unit.

8. A device for monitoring an amount of fluid in a hydration unit, comprising:
   a monitoring unit comprising a fluid chamber, an inlet port attachable to a fluid outlet of a hydration unit, and an outlet port for attachment to a feed tube;
   a pressure sensor mounted to the monitoring unit and in pressure communication with the fluid chamber;
   a tilt sensor mounted to the monitoring unit, the tilt sensor being operable to determine angle of tilt of the hydration unit;
   a controller mounted to the monitoring unit and connected to the pressure sensor for obtaining a pressure sensor signal therefrom, the controller being operable to determine from the pressure sensor signal an indication of volume of fluid in the hydration unit and to compensate a deviation in pressure measurements caused by a tilt of the hydration unit; and
   a valve that prevents back pressure from being introduced into the chamber from a feed tube, the valve being disposed in the monitoring unit and being electronically controlled by the controller.

9. The device of claim 8, wherein the controller comprises a database of calibration values for calibrating the indication of volume derived from sensed pressure.

10. The device of claim 8, wherein the controller is operable to obtain a sequence of pressure measurements and to determine therefrom a fluid consumption.

11. The device of claim 8, further comprising a communications unit connected to the controller and operable to send data to the controller or receive data from the controller.

12. The device of claim 8, wherein the inlet port is a replaceable adaptor adapted to fit different configurations of the hydration unit.

13. The device of claim 8, further comprising a connection hose for coupling between the inlet port of the monitoring unit and the outlet port of the hydration unit.

14. The device of claim 8, wherein the inlet port comprises a first tubular element, the first tubular element comprising an internal diameter adapted to fit over the outlet port of the hydration unit.

15. The device of claim 8, wherein the monitoring unit is integral with the hydration unit.

16. A method for monitoring an amount of fluid in a hydration unit having a fluid outlet, comprising:
   providing a monitoring unit, the monitoring unit comprising:
     a fluid chamber;
     an inlet port attachable to a fluid outlet of a hydration unit;
     an outlet port for attachment to a feed tube;
     a pressure sensor mounted to the monitoring unit and in pressure communication with the fluid chamber; and
     a tilt sensor operable to determine an angle of tilt of the hydration unit;
   obtaining, by a controller coupled to the pressure sensor and the tilt sensor, a pressure sensor signal from the pressure sensor and the angle of tilt from the tilt sensor;
   determining, by the controller, a volume of fluid in the hydration unit based on the pressure sensor signal;
   calibrating, by the controller, pressure measurements based on the angle of tilt; and
   providing, in a display, an indication of the volume of fluid in the hydration unit; and
   providing a valve configured to prevent back pressure from being introduced into the chamber from a feed tube, the valve being disposed in the monitoring unit and being electronically controlled by the controller.

17. The method of claim 16, further comprising:
obtaining, by the controller, a sequence of pressure measurements; and
determining, by the controller, a fluid consumption based on the sequence of pressure measurements.

18. The method of claim 16, further comprising providing a connection hose that couples between the inlet port of the monitoring unit and the outlet port of the hydration unit.

19. The method of claim 18, wherein the inlet port comprises a first tubular element, the first tubular element comprising an internal diameter adapted to fit over the outlet port of the hydration unit.

20. The method of claim 16, wherein the monitoring unit is integral with the hydration unit.

\* \* \* \* \*